(12) United States Patent
Muthu

(10) Patent No.: US 10,955,687 B2
(45) Date of Patent: Mar. 23, 2021

(54) BIOMEDICAL DEVICE INCLUDING ENCAPSULATION

(71) Applicant: Johnson & Johnson Vision Care, Inc., Jacksonville, FL (US)

(72) Inventor: Milburn Muthu, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 14 days.

(21) Appl. No.: 15/655,361

(22) Filed: Jul. 20, 2017

(65) Prior Publication Data

US 2018/0024379 A1 Jan. 25, 2018

Related U.S. Application Data

(60) Provisional application No. 62/365,248, filed on Jul. 21, 2016.

(51) Int. Cl.
| | |
|---|---|
| *G02C 7/02* | (2006.01) |
| *G02C 7/04* | (2006.01) |
| *B29D 11/00* | (2006.01) |
| *A61L 31/08* | (2006.01) |
| *A61L 27/30* | (2006.01) |

(Continued)

(52) U.S. Cl.
CPC ............ *G02C 7/041* (2013.01); *A61L 27/30* (2013.01); *A61L 31/082* (2013.01); *B29D 11/00038* (2013.01); *B29D 11/00817* (2013.01); *G02C 7/049* (2013.01); *A61L 2430/16* (2013.01); *A61N 1/375* (2013.01); *G02C 7/04* (2013.01); *G02C 7/083* (2013.01)

(58) Field of Classification Search
CPC ........ G02C 7/041; G02C 7/049; G02C 7/083; G02C 7/04; G02C 7/00; G02C 2200/00; A61L 2430/16; A61L 31/082; A61L 27/30; A61L 2300/608; A61N 1/375; A61N 1/37211; B29D 11/00817; B29D 11/00038
USPC ..................................................... 351/159.01
See application file for complete search history.

(56) References Cited

U.S. PATENT DOCUMENTS

| | | | |
|---|---|---|---|
| 10,001,661 B1 * | 6/2018 | Weibel | .................... G02C 7/12 |
| 2011/0270028 A1 | 11/2011 | Honaryar | |

(Continued)

FOREIGN PATENT DOCUMENTS

| | | | |
|---|---|---|---|
| EP | 2600702 A2 | 6/2013 | |
| WO | WO 2010057095 A2 | 5/2010 | |

(Continued)

OTHER PUBLICATIONS

PCT Search Report —For Application No. PCT/US2017/043171 dated Oct. 23, 2017.

*Primary Examiner* — William R Alexander
*Assistant Examiner* — Henry A Duong

(57) ABSTRACT

A biomedical device including an energy source, an electro-active device operatively connected to the energy source, circuitry configured to control operation of the electro-active device, at least one barrier layer including at least one inorganic material surrounding the energy source, electro-active device and circuitry, and at least one molded layer surrounding the at least one barrier layer. A method for encapsulating electronic components of an electro-active biomedical device in a protective envelope containing a barrier layer including at least one inorganic compound, and a molded polymer overcoat.

13 Claims, 4 Drawing Sheets

(51) Int. Cl.
G02C 7/08 (2006.01)
A61N 1/375 (2006.01)

(56) References Cited

U.S. PATENT DOCUMENTS

2014/0200424 A1\* 7/2014 Etzkorn ............. A61B 5/14532
 600/345
2015/0362752 A1\* 12/2015 Linhardt ................ G02C 7/083
 349/13

FOREIGN PATENT DOCUMENTS

WO WO 201101870 A2 2/2011
WO WO 2015041944 A1 3/2015

\* cited by examiner

BIOMEDICAL DEVICE INCLUDING ENCAPSULATION

CROSS-REFERENCE TO RELATED APPLICATIONS

This application claims the benefit of U.S. Provisional Application No. 62/365,248 filed Jul. 21, 2016, the contents of which is incorporated by reference herein in its entirety.

FIELD OF THE INVENTION

The invention relates to biomedical devices. In particular, the invention relates to biomedical devices including an encapsulation to protect the biomedical devices from contact with bodily fluids. The encapsulation may also protect a user from exposure to components of the biomedical device.

BACKGROUND OF THE INVENTION

Advances in medical devices have produced smaller and more complex medical devices. Medical devices may incorporate powered functional components and a power source. The powered components may include control elements incorporated in semiconductor chips, among other things. Examples of such devices may include implantable pacemakers, micro-energy harvesters, electronic pills for monitoring and/or testing biological functions, surgical devices with active components, ophthalmic devices, contact lenses, infusion pumps, defibrillators, stents, and neurostimulators. Some of these devices are implantable, such as pacemakers, while others may contact tissue in some way for short or long periods of time, such as a surgical instrument or contact lens, respectively.

Regardless of whether they are powered or not, medical devices need to be biocompatible. However, introducing a power source and functional components into medical devices results in the need to protect them from bodily fluids as well as to protect a user or patient from coming into contact with the power source or functional elements. For example, a pacemaker and surgical instruments could contact blood and interstitial or other fluids; and a contact lens could contact tears or mucus. Contact with bodily fluids could short out a power source and render functional components of medical devices inoperable. Conversely, contact of bodily fluids with, for example, anode or cathode material, could be harmful to a user or patient.

SUMMARY OF THE INVENTION

The present invention is directed to encapsulating electronic components of a biomedical device, such as a contact lens, in a protective envelope such that the biomedical device is able to withstand conditions to which it is exposed during its manufacture and/or normal use.

An embodiment of the invention includes a biomedical device, such as a contact lens, including an energy source, an electro-active device operatively connected to the energy source, integrated circuitry configured to control operation of the electro-active device, one or more barrier layers comprising an inorganic material surrounding the energy source, electro-active device and integrated circuitry, and one or more molded layers surrounding the barrier layer(s). At least a portion of an external contour of the molded layer(s) may substantially correspond to at least a portion of a desired external contour of the biomedical device. The electro-active device of the biomedical device may comprise a liquid crystal variable optic. Also, the molded layer(s) of the biomedical device may comprise one or more cast molded polymers.

The biomedical device may also include one or more first conformal coatings between the barrier layer(s) and the energy source, electro-active device and integrated circuitry, and/or one or more second conformal coating between the barrier layer(s) and the molded layer(s). The biomedical device may further include a coating layer on the outer surface of the molded layer(s), and/or an embedment surrounding the molded layer(s).

Another embodiment of the invention includes a method for encapsulating electronic components of an electro-active biomedical device, such as a contact lens, in a protective envelope. The method includes applying one or more barrier layers comprising at least one inorganic compound to surround the electro-active biomedical device, and surrounding the barrier layer(s) with one or more molded polymer layers. The electronic components included in the method may comprise a liquid crystal variable optic, and the molded polymer layer(s) may comprise a cast molded polymer.

The method may also include applying one or more first conformal coatings between the barrier layer(s) and the electronic components, and/or applying one or more second conformal coatings between the barrier layer(s) and the molded polymer layer(s). The method may further include applying a coating layer over the molded polymer layer(s), and/or forming an embedment surrounding the molded polymer layer(s).

Still other objects and advantages of the present invention will become readily apparent by those skilled in the art from the following detailed description, wherein is shown and described only the preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the drawings and description are to be regarded as illustrative in nature and not as restrictive.

BRIEF DESCRIPTION OF THE DRAWINGS

The above-mentioned objects and advantages of the present invention will be more clearly understood when considered in conjunction with the accompanying drawings, in which.

DETAILED DESCRIPTION OF EMBODIMENTS OF THE INVENTION

Figure 1:
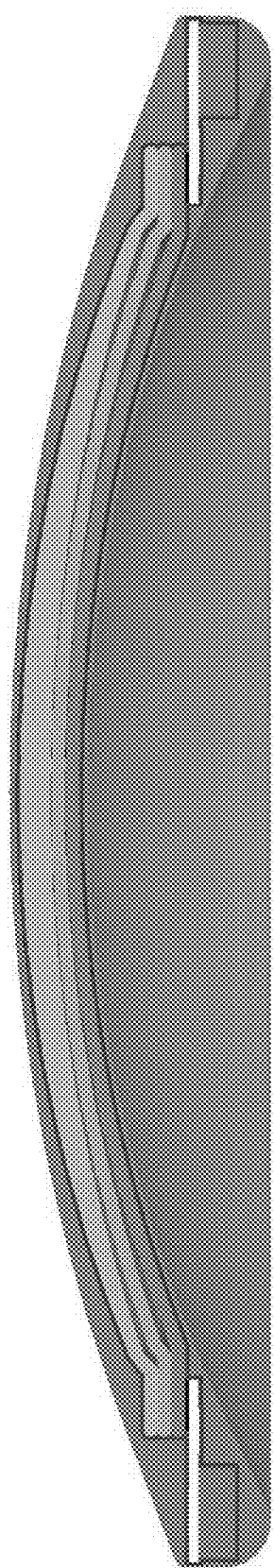
FIG. 1 represents a cross-sectional view of an embodiment of the invention comprising an electro-active insert for a contact lens.

A biomedical device has a function. The construction of the device supports this function. To be able to carry out the function, the biomedical device should be compatible with the human body. When the powered components and power source are incorporated into a biomedical device, issues arise with preventing damage to the powered components and power source from bodily fluids as well as harm to the human body from contact with the powered components and power source. Any protection for the biomedical device and/or the body must still permit the biomedical device to function normally.

In the case of biomedical devices undergoing sustained contact with the human body, such as pace makers and contact lenses, it may be important that the powered components and power source are protected for an extended period of time. For example, a contact lens may need to protect the powered components and power source for at least 3 years. A pace maker may require protection for even longer.

An overmold or encapsulation structure may protect a biomedical device and the body with which the device is utilized and permit the biomedical device to function. Embodiments of an overmold structure may include one or more layers or other components. The layer(s) may have different compositions and functions and may or may not entirely surround the biomedical device. A composition of a component of the overmold may affect the characteristics of that component. In some embodiments the overmold does not form the exterior surface of the biomedical device, but is rather embedded in the biomedical device.

Additionally, an overmold may need to be moldable to a specific shape for a particular use of a biomedical device. Another factor affecting the composition of components of the overmold is compatibility with each other and with other parts of the biomedical device. Typically, the overmold or components thereof provide a chemical, electrical, and/or moisture resistant barrier. As such, the overmold protects the electronic components and power source of the biomedical device.

Similarly, the construction of the biomedical device should withstand conditions to which the device is exposed during use. While this may include exposure to bodily fluids, it may also include exposure to disinfection and sterilization processes carried out prior to use. Also, biomedical devices such as contact lenses may be periodically subject to cleaning and sterilization, such as through chemical treatment and/or the application of heat or radiation. The biomedical device should be able to withstand such treatment as necessary.

As an example, a contact lens including electo-active functional components and geometries is discussed herein. However, the structure of the overmold may be applied to any biomedical device. For example, the overmold/encapsulation could be applied to implantable pacemakers, micro-energy harvesters, electronic pills for monitoring and/or testing biological functions, surgical devices with active components, ophthalmic devices, contact lenses, infusion pumps, defibrillators, stents, and neurostimulators. Any device that may be exposed to bodily fluid for a period of time may beneficially include coatings and overmold/encapsulation as described herein.

Not all contact lenses or other biomedical devices need to include all components of the overmold. Additionally, compositions of various components of the overmold may vary, depending on the structure, composition, use and/or environment of the device. For example, in the context of a contact lens, the overmold typically has optical properties that do not interfere with the contact lens function.

First Conformal Coating

An electro-optic biomedical device, such as an electronically controlled variable focus contact lens, may include a power source, electronic control components and optic elements. All of these elements may be surrounded by one or more first conformal coatings. This first conformal coating(s) (as discussed below, the structure may include other conformal coatings) typically provide a smooth surface for the application of one or more barrier coatings. Along these lines, the first conformal coating(s) may eliminate sharp edges or corners of the power source, electronic control components and optic elements to facilitate the application of one or more barrier layers thereto. Spray, dip, or other conventional coating methods may be utilized to apply the first conformal coating(s). The first conformal coating(s) should be applied in an amount sufficient to promote coverage of the electronic components with one or more barrier layers as described below. Typically, the thickness of the first conformal coating(s) is in the range of from about 1 um to about 100 um. More typically, the thickness of the first conformal coating(s) is in the range of from about 5 um to about 10 um.

The first conformal coating(s) typically comprise one or more hydrophobic polymer(s). Suitable hydrophobic polymers generally include acrylics, amides, imides, carbonates, dienes, esters, ethers, fluorocarbons, olefins, styrenes, vinyl acetals, vinyl and vinylidene chlorides, vinyl esters, vinyl ethers and ketones, vinylpyridine and vinypyrrolidone polymers. Combinations of such hydrophobic polymers may also be used.

The polymer(s) preferably have a water vapor transmission rate (WVTR) in the range of from about 0.001 $g/m^2/day$ to about 100 $g/m^2/day$. Typically, the WVTR is in the range of from about 1 $g/m^2/day$ to about 20 $g/m^2/day$. Similarly, to maximize shelf life, the water uptake of the polymer(s) should be low. Typically, the water uptake of the polymer(s) is less than about 0.01% after 7 days at room temperature.

The polymer(s) utilized in the first conformal coating(s) may depend upon the function of the biomedical device. For example, if the biomedical device is a contact lens, then the polymer(s) should have suitable optical transmission properties. Such polymer(s) preferably have an optical transmission of about 80% or more of visible light. Typically, the optical transmission is about 85% or more. More typically, the optical transmission is about 90% or more. Along these lines, the polymer(s) preferably have a refractive index in the range of from about 1.2 to about 1.8. Typically, the refractive index is in the range of from about 1.4 to about 1.6. Exemplary polymers having optical transmission and refractive indices within these ranges include Epotek 301; Epotek 301-2; Nusil Med 10-6010; Epotek OG 603; Epotek OG 142-95; Epotek OG 142-112; Norland optical adhesives 61; Norland optical adhesives 68; Norland optical adhesives 86; Momentive UV LSR 2060; Momentive LSR 7070; Momentive RTV 615; and paralyne.

Furthermore, the polymer(s) utilized in the first conformal coating(s) preferably have an Abbe number of about 30 or more. Typically, the Abbe number is about 40 or more. Additionally, the polymer(s) advantageously have a haze value of about 10% or less. Typically, the haze value is about 2% or less. Also, the polymer(s) desirably have a b value based on L-A-B color space measurement of 10% or less. Typically, the b value is 3% or less.

Prior to applying the first conformal coating(s), it may be necessary or desirable to apply a pretreatment to the electronic components to help ensure that the first conformal coating(s) adheres thereto. Examples of such pretreatments could include one or more processes to remove any surface contamination or irregularities, or to create a desirable surface texture. For example, grinding, turning, and/or other processes could be utilized. Additionally, one or more processes may be carried out to degrease the substrate. For example, a dissolvent bath, steam cleaning, ultrasonic cleaning, plasma cleaning, and/or other processes could be utilized. Furthermore, blast cleaning may be utilized to increase the surface roughness. Any one or more of these processes could be utilized. Alternatively, no process may be needed or desired to increase adhesion of the first conformal coating(s).

Barrier Layer

The power source, electronic control components and optic elements, with or without the first conformal coating(s), may be at least partially surrounded by one or more barrier layers. The barrier layer(s) provide a water vapor barrier that reduces the rate of water vapor transmission through the composite coatings forming the overmold. However, the barrier layer(s) may have other additional or alternative functions. The barrier layer(s) should be free of defects such as pin-holes and other known defects that may commonly occur during thin film deposition processes.

The thickness of the barrier layer(s) may vary. For example, the thickness may commonly be in the range of from about 1 nm to about 1 mm. Typically, the thickness is in the range of from about 10 nm to about 500 nm. More typically, the thickness is in the range of from about 30 nm to about 200 nm. Particular embodiments include barrier layer thicknesses of 50 nm, 100 nm and 200 nm.

To protect the functionality of the power source, electronic components and optic elements, the barrier layer(s) should have a water vapor transmission rate (WVTR) in the range of from about 1 to about $10^{-6}$ g/m$^2$/day. Typically, the WVTR is in the range of from about $10^{-2}$ to about $10^{-6}$ g/m$^2$/day. More typically, the WVTR is in the range of from about $10^{-4}$ to about $10^{-6}$ g/m$^2$/day.

A variety of materials may be utilized in the barrier layer(s). Useful materials should be compatible with the underlying power source, electronic control components and optic elements, any conformal coatings applied thereto, as well as the one or more molded polymer layer(s). Typically, the materials of the barrier layer(s) also have a strong adhesion to the first conformal coating(s) or, in the absence of the first conformal coating(s), to the underlying power source, electronic control components and optic elements that may be utilized to form the electro-active optic portion of the lens.

Typically, the barrier layer(s) comprise one or more inorganic materials. The inorganic material(s) provide water vapor protection for the power source, electronic control components and optic elements by reducing the WVTR. Suitable inorganic material(s) for the barrier layer(s) may include one or more of $Al_2O_3$; $TiO_2$; $Ta_2O_5$; $Nb_2O_5$; $HfO_2$; $ZrO_2$; $SiO_2$; ZnO; MgO; $Ga_2O_3$; $La_2O_3$; $Y_2O_3$; $Yb_2O_3$; $Sc_2O_3$; $Er_2O_3$; $V_2O_5$; $CeO_2$; CaO; or CuO. Typically, inorganic material(s) of the barrier layer(s) include one or more of $Al_2O_3$, $SiO_2$, and/or $TiO_2$. For optical applications, inorganic material(s) that are sufficiently transparent should generally be utilized, such as one or more of $Al_2O_3$, $SiO_2$, and $TiO_2$.

If the biomedical device is a contact lens, then the material(s) selected for the barrier layer(s) is preferably optically clear. Along these lines, the barrier layer(s) advantageously have a refractive index in the range of from about 1.1 to about 2.95. Typically, the refractive index is in the range of from about 1.4 to about 1.7. More typically, the refractive index is in the range of from about 1.4 to about 1.6. Furthermore, the barrier layer(s) desirably have an optical transmission in the range of from about 60% to about 100%. Typically, the optical transmission is in the range of from about 80% to about 100%. More typically, the optical transmission is in the range of from about 85 to about 99%. Suitable inorganic materials that meet these requirements include one or more of $Al_2O_3$, $SiO_2$, and $TiO_2$.

Various methods may be utilized to deposit the barrier layer(s). For example, chemical vapor deposition (CVD), physical vapor deposition (PVD) or atomic layer deposition (ALD) may be utilized to deposit the barrier layer(s). Other methods could include spray coating, dip coating, spin coating, or other types of coating. Typically, the barrier layer(s) is deposited or formed at a temperature of about 20° C. to about 500° C. More typically, the barrier layer(s) are formed at a temperature of about 20° C. to about 60° C.

The process may be carried out at sub-atmospheric pressures. For example, the process could be carried out at a pressure in the range of from about 500 millitorr to about 760 torr. Typically, the process of forming the barrier layer(s) is carried out at a pressure in the range of from about $10^{-2}$ mbar to about $10^{-8}$ mbar.

Prior to applying the barrier layer(s) to the electronic components and/or first conformal coating(s), it may be necessary or desirable to apply a pretreatment to the electronic components and/or first conformal coating(s) to help ensure that the barrier layer(s) adhere. Examples of such pretreatments could include one or more processes to remove any surface contamination or irregularities, and/or to create a desirable surface texture. For example, grinding, turning, and/or other processes could be utilized.

Additionally, one or more processes may be carried out to degrease the substrate. For example, prior to applying the barrier layer(s) to the electronic components, a dissolvent bath, steam cleaning, ultrasonic cleaning, plasma cleaning, and/or other processes could be utilized. Conversely, prior to applying the barrier layer(s) to the first conformal coating(s), an oxidizing cleaning, an oxygen plasma cleaning, a UV-ozone cleaning, and/or in-situ $O_2$-plasma cleaning could be utilized. Furthermore, blast cleaning may be utilized to increase the surface roughness. Any one or more of these processes could be utilized. Alternatively, no process may be needed or desired to increase barrier adhesion.

Second Conformal Coating

After applying the barrier layer(s), one or more second conformal coatings may be applied to at least partially surround the barrier layer(s). The second conformal coating(s) may protect the barrier layer(s) during handling of the structure. The second conformal coating(s) may also reduce variations in the surface of the structure after application of the barrier layer(s).

The second conformal coating(s) generally should have a thickness sufficient to reduce surface variations in the barrier-coated structure to a desired degree, and/or to provide a desired degree of protection. Typically, the second conformal coating(s) have a thickness in the range of from about 500 nm to about 1 mm. More typically, the second conformal coating(s) have a thickness in the range of from about 1 μm to about 20 μm. Most typically, the second conformal coating(s) have a thickness in the range of from about 1 μm to about 10 μm.

The materials utilized in the second conformal coating(s) may be the same, or substantially the same, as the materials mentioned above for the first conformal coating(s). For instance, if the biomedical device is contact lens, the polymers utilized in the second conformal coating(s) desirably have the same characteristics as the materials used in the first conformal coating(s) mentioned above. Along these lines, the properties of the polymers utilized in the second conformal coating(s) (i.e., the optical transmission, refractive index, Abbe value) may be the same or substantially the same as those properties mentioned above for the polymers utilized in the first conformal coating(s). Preferably the same materials are used in both the first and second conformal coating(s) to reduce any internal stresses due to thermal expansion and contraction.

Molded Layer

After applying the barrier layer(s) and any first and second conformal coating(s), one or more molded layers may be formed around at least a portion of the entire structure. Typically, the molded layer(s) surround the entire structure and have an exterior contour that is compatible with the desired shape of the biomedical device. For example, if the biomedical device is a contact lens, the molded layer(s) may have a shape similar to the shape of the contact lens. Other biomedical devices may have other shapes. It may also be possible for the molded layer(s) to have an outer shape that has no relationship to a functional aspect of the biomedical device, unlike a contact lens.

The materials utilized in the molded layer(s) should be the same or substantially the same to those of the first and/or second conformal coating(s). By using the same or substantially the same materials, the molded layer(s) will have a thermal expansion coefficient that is the same or very close to that of the first and/or second conformal coating(s), which may help retain interlayer adhesion. However, to the extent that the molded layer(s) and first and second conformal coating(s) comprise different materials, such materials should nonetheless have sufficiently similar thermal expansion coefficients to prevent delamination at temperatures to which the device is exposed during manufacture, storage and use.

The materials used in the molded layer(s) typically include one or more polymers. Any of the polymer(s) described above with respect to the first and/or second conformal coating(s) may also utilized in the molded layer(s). For instance, like the polymer(s) of the first and/or second conformal coating(s), the polymer(s) of the molded layer(s) may be hydrophobic. In addition, the polymer(s) included in the first and/or second conformal coating(s), barrier layer(s), and molded layer(s) may be selected based upon compatibility with each other, thermal expansion properties and/or surface adhesion characteristics, among other factors.

With any biomedical device, the polymer(s) of the molded layer(s) should be biocompatible. Moreover, the polymer(s) of the molded layer(s) should also be compatible with substances with which the polymer(s) may contact during use of the device. For instance, in the context of a contact lens, typically, the polymer(s) should be compatible with lens cleaning solution, mild acid disinfectant, and common organic solvents.

The polymer(s) of the molded layer(s) preferably have a low water vapor transmission rate (WVTR). Along these lines, the WVTR of the polymer(s) is typically in the range of from about 0.001 g/m$^2$/day to about 100 g/m$^2$/day. More typically, the WVTR is in the range of from about 1 g/m$^2$/day to about 10 g/m$^2$/day. Similarly, to maximize shelf life, the water uptake of the polymer(s) should be low. Typically, the water uptake of the polymer(s) is less than about 0.01% after 7 days at room temperature.

Also, like the polymer(s) utilized in the first and/or second conformal coating(s), the polymer(s) utilized in the molded layer(s) may depend upon the function of the biomedical device. Along these lines, when the biomedical device is a contact lens, the polymer(s) of the molded layer(s) may desirably have the same, or substantially the same, optical transmission and refractive index as those utilized in the first and/or second conformal coating(s). Similarly, the Abbe number, b value and haze value of the polymer(s) of the molded layer(s) may also be the same, or substantially similar, to those of the polymer(s) of the first and/or second conformal coating(s).

In some cases, one or more additive(s) may be added to the polymer(s) or polymer mixtures for various reasons. For example, the additive(s) may improve mechanical strength and/or water uptake properties of the polymer(s). As such, if hydrophobic polymer(s) are used in the molded layer(s), the additives may improve its hydrophobic nature.

Physical attributes of the polymer(s) may vary depending upon the application. For example, if the biomedical device is a contact lens, the polymer(s) may be softer. Alternatively, if the biomedical device is a pacemaker, the polymer(s) may be harder. Typically, the molded layer(s) of a contact lens have a Shore D hardness greater than about 40D. More typically, the molded layer(s) of a contact lens have a Shore D hardness greater than about 65D.

The physical characteristics of the polymer(s) may also depend upon the composition of the barrier layer(s), first and second conformal coating(s), and/or any other layers applied over the molded layer(s). For example, when the biomedical device is a contact lens, it is desirable for the polymer(s) of the molded layer(s) to have a strong adhesion to hydrogel, which forms the outermost layer of the contact lens. Along these lines, when the biomedical device is a contact lens, it is also desirable for the polymer(s) of the molded layer(s) to be compatible with TOPAS, polypropylene, polyimide, polyethylene, and/or other materials utilized to make contact lenses.

The polymer(s) making up the molded layer(s) may have any suitable form. However, they typically are liquid prior to curing. If the polymer(s) are liquid, they typically have a viscosity in the range of from about 10 to about 500000 CP. More typically, the viscosity is in the range of from about 10 CP to about 100000 CP. Most typically, the viscosity is in the range of from about 10 CP to about 1000 CP. The viscosity may be adjusted by adding suitable solvents.

A liquid polymer may permit the molded layer to be cast in a mold. For example, polymer may be introduced into a lower mold portion, the barrier coated electronics arranged on the polymer. Then, additional polymer may be added to the lower mold to cover the barrier coated electronics. An upper mold portion may then cover the polymer to shape the upper surface of the polymer. The mold may have a desired shape, such as a contact lens shape, depending upon the biomedical device being fabricated.

After the polymer(s) and electronics are arranged in the mold, the polymer(s) may be cured utilizing a variety of different techniques. such as heat and/or electromagnetic radiation. If heat is utilized to cure the polymer(s), the temperature carried out should be such that it does not damage the underlying elements and/or the underlying layers. Along these lines, the curing is typically carried out at a temperature below about 80° C. More typically, the curing is carried out at a temperature below about 50° C. Most typically, the curing is carried out at a minimum of about 20° C.

Alternatively, if electromagnetic radiation is utilized, it may have wavelengths from ultraviolet to visible light. In other words, the radiation may have a wavelength in the range of from about 10 nm to about 710 nm. Typically, ultraviolet radiation having a wavelength in the range of from about 420 nm to about 460 nm is useful. According to specific embodiments, wavelengths of 420 nm, 435 nm, or 460 nm are utilized.

Combinations of radiation and heat may also be utilized. Along these lines, according to one embodiment, the UV radiation applied should be under conditions of about 60° C. Other techniques that may be utilized include thermal curing, three-dimensional printing, or other similar molding or curing methods. The entire structure could be cured at once or spot curing could be utilized.

The curing time may depend upon the polymer(s) utilized, the method of cure and the temperature. The cure time may depend upon the desired degree of polymerization. As with the temperature, the curing time should be less than a period that would damage powered functional components. At a temperature of about 60° C. and below, the curing time may be about 24 hours to about 96 hours. If the temperature is about 90° C. or below, the curing time may be less than about 30 minutes. If the temperature is about 100° C. or above, the curing may be carried out for about 5 minutes or less. Each layer of the structure may be at least partially cured prior to applying any additional layers. Conversely, each layer may be fully cured prior to applying any additional layers. Typically, the molding and curing processes may be carried out at atmospheric pressure.

After curing the polymer(s), the polymer coated structure may be further processed. Such further processing can include direct incorporation into a biomedical device, or the application of additional coating layers or surface modification techniques as desired. For example, if the biomedical device is a contact lens, one or more adhesion promotion layers may be applied around at least a portion of the molded layer(s) to enhance the adhesion of hydrogel thereto. The adhesion promotion layer(s) may comprise a liquid primer. The adhesion promotion layer(s) may be applied by spray coating, spin coating, dip coating, and other similar types of coating processes.

Similarly, if the biomedical device is a contact lens, the molded layer(s) may be treated with plasma, UV, or corona to create surface groups and utilize them to enhance adhesion of hydrogel thereto. An exemplary process includes an $O_2$ plasma treatment followed by a Silane chemistry treatment and encapsulation of a hydrogel.

Additionally, when the biomedical device is a contact lens, the shrinkage of the polymer(s) during the molding process should be as minimal as possible. Typically, the shrinkage of the polymer(s) is about 20% or less. More typically, the shrinkage of the polymer(s) is about 5% or less. Most typically, the shrinkage of the polymer(s) is about 2% or less. Additionally, electrical resistivity of the polymer(s) typically is as large as possible. Along these lines, the resistivity is typically multiple megaohms, such as at least about $10^{12}$ Ω-cm.

According to some embodiments, the structure, including the molded polymer layer(s), may be the final form of the biomedical device. Other embodiments may include additional structure surrounding the molded layer(s). For example, if the biomedical device is a contact lens, then the molded layer(s) may be surrounded by a typical hydrogel embedment. Methods for forming the hydrogel embedment are known and need not be described in detail.

Figure 2:
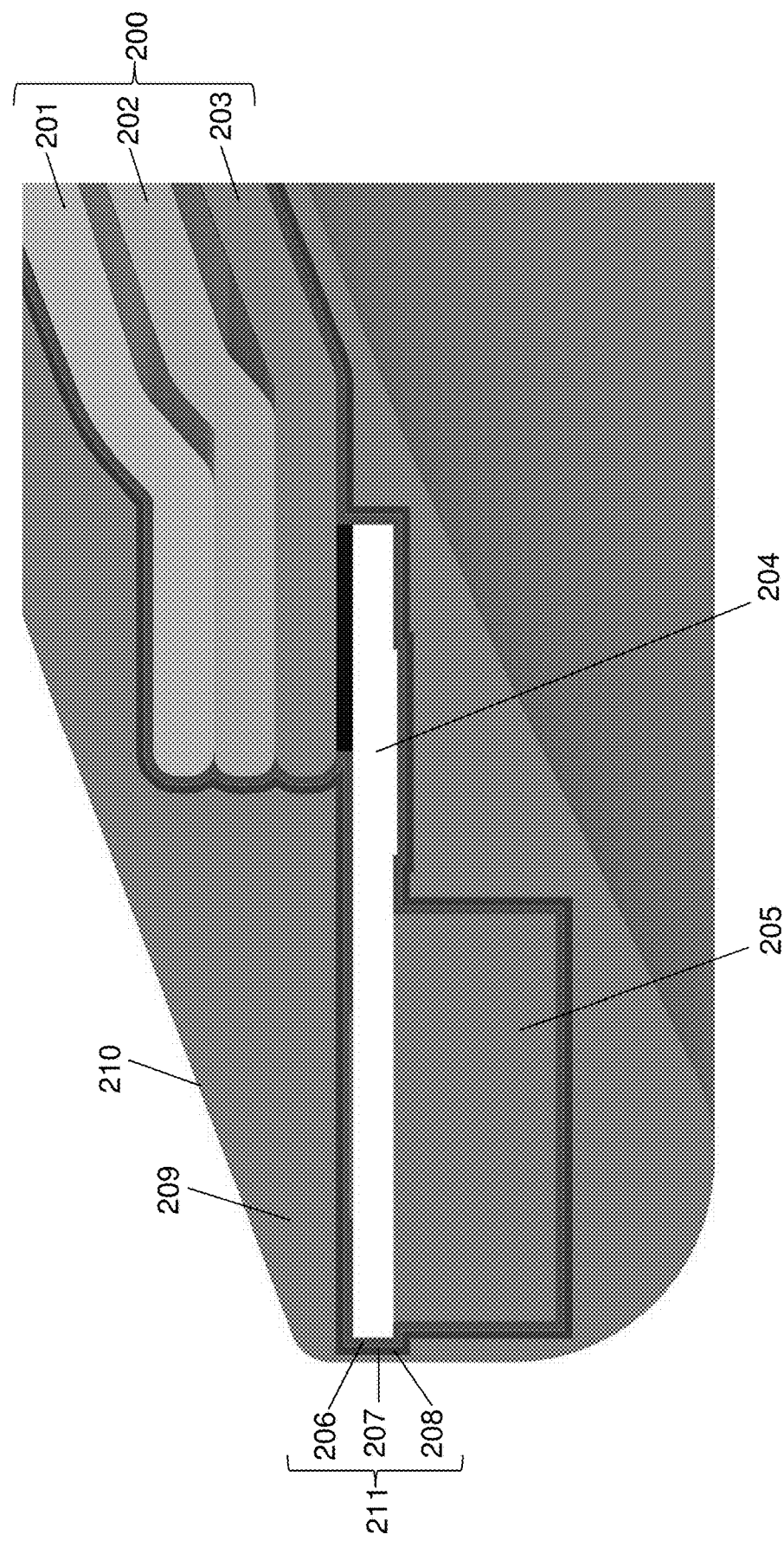
FIG. 2 represents a close-up cross-sectional view of a portion of the embodiment shown in FIG. 1.

FIGS. 1 and 2 are cross-sectional views of an embodiment of encapsulation layers for a powered contact lens insert. Along these lines, FIG. 1 is a cross-sectional view of the powered components and power source of the insert enveloped in an embodiment of the encapsulation. FIG. 2 is a close-up cross sectional view of a portion of the embodiment shown in FIG. 1 illustrating the multi-layer composite structure of the overmold encapsulation. The powered contact lens may include an optical component 200, integrated circuitry 204, and a power source 205, such as a micro-battery. The optical component 200 may comprise a front optic 201, a middle optic 202, a back optic 203. According to some embodiments, the front optic 201, middle optic 202, and back optic 203 may include cyclic olefin copolymer. Alternatively, the optical component 200 may comprise a liquid meniscus lens comprising two immiscible fluids. Additionally, the integrated circuitry 204 may include a silicon-based chip. Furthermore, an outer-most layer of the power source 205 may include metal interconnects, such as brass or titanium, or a polymer film capable of sealing. Along these lines, the integrated circuitry 204 and power source 205 may be located outside of an optical zone of the contact lens that the wearer looks through. The embodiment shown in FIGS. 1 and 2 includes a first conformal coating 206, a barrier layer 207, a second conformal coating 208, a molded polymer layer 209, and a surface coating 210. These various layers may be referred to collectively as an encapsulation layer 211.

Figure 3:
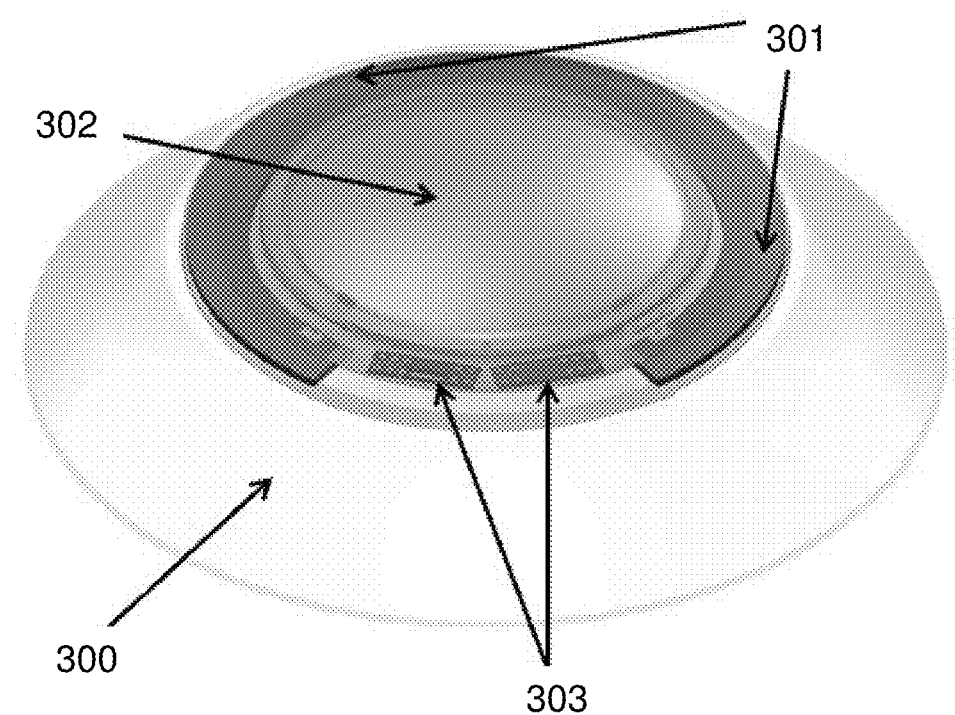
FIG. 3 represents a perspective view of an electro-active contact lens.

FIG. 3 represents a perspective view of an entire contact lens that includes an electro-active lens insert comprising hydrogel layer 300 surrounding an insert containing power source 301 and a plurality of other components, such as integrated circuitry 303 and optical component 302. The power source 301 may be in the shape of an annulus or a portion of an annulus.

Figure 4:
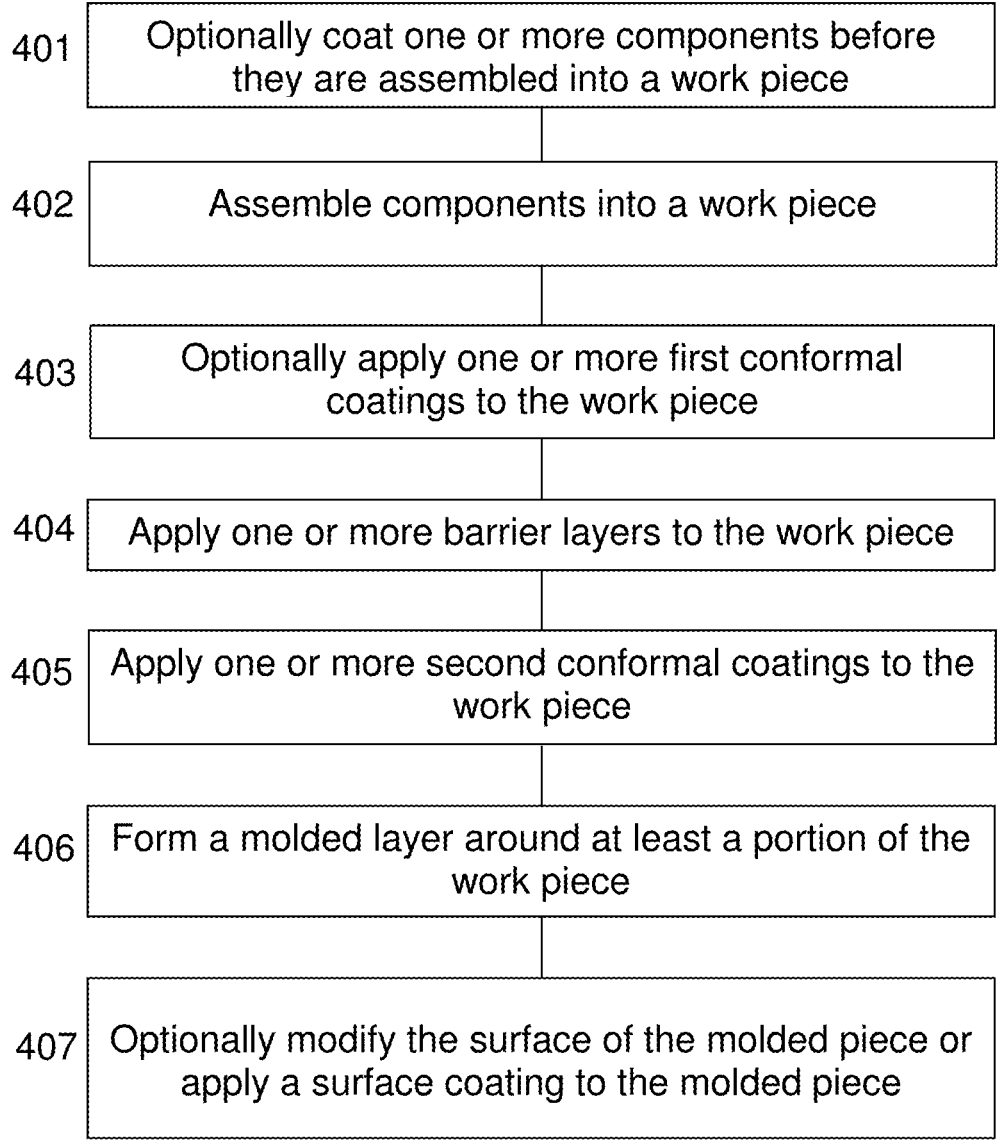
FIG. 4 represents a flowchart illustrating an embodiment of a method for forming a biomedical device with a protective encapsulation.

FIG. 4 provides a flowchart illustrating elements of an embodiment of an overmolding process as described above, and as used, for example, in processes where the biomedical device to be formed is a powered contact lens. The process may begin with an optional step 401 to coat one or more components before they are assembled into a work piece. According to some embodiments, the components may include: a power supply, support substrates on which to mount various components, interconnect features to provide electrical interconnection between the various components, electrical circuit components, such as integrated circuits and passive electrical devices, and electro-active elements, such as electro-active optical focal power modifying components. Each component may be formed with a different type of surface layer and may require a coating to align the respective surface characteristics with the rest of the overmold processing. The various components may be assembled 402 into a work piece.

Thereafter, the process may continue to step 403 to apply one or more first conformal coatings to at least a portion of the work piece. One or more barrier coatings may then be deposited, at step 404, to at least a portion of the work piece. Subsequently, at step 405, one or more second conformal coatings may be applied to at least a portion of the work piece. The second conformal coating(s) may comprise materials that are the same or substantially the same as those of the first conformal coating(s). At step 406, one or more molded layers may be formed around at least a portion of the work piece. The molded layer(s) may partially or entirely surround the work piece and be formed to an exterior contour compatible with the desired shape of the resulting biomedical device. The resulting molded piece may be further processed to make a biomedical device of various kinds, such as a contact lens. Optionally, at step 407, the resulting molded piece may be subject to treatments to modify its surface, such as plasma treatments, so that it is compatible with further processing. Alternatively, an additional layer may be applied to the resulting molded piece to provide desired surface characteristics.

The foregoing description of the invention illustrates and describes the present invention. The disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. Accordingly, the description is not intended to limit the invention to the form of the best modes of practicing the invention disclosed herein, and it is intended that the appended claims be construed to include alternative embodiments.

The invention claimed is:

1. A biomedical device, comprising:
   an energy source;
   an electro-active device operatively connected to the energy source;
   circuitry configured to control operation of the electro-active device;
   a barrier layer comprising an inorganic material surrounding the energy source, the electro-active device, and the circuitry; and
   a molded layer surrounding the barrier layer.

2. The biomedical device according to claim 1, wherein the inorganic material comprises at least one of $Al_2O_3$, $TiO_2$, $Ta_2O_5$, $Nb_2O_5$, $HfO_2$, $ZrO_2$, $SiO_2$, $ZnO$, $MgO$, $Ga_2O_3$, $La_2O_3$, $Y_2O_3$, $Yb_2O_3$, $Sc_2O_3$, $Er_2O_3$, $V_2O_5$, $CeO_2$, $CaO$, or $CuO$.

3. The biomedical device according to claim 1, wherein the barrier layer has a thickness of about 50 nm to about 200 nm.

4. The biomedical device according to claim 1, wherein at least a portion of an external contour of the molded layer substantially corresponds to at least a portion of a desired external contour of the biomedical device.

5. The biomedical device according to claim 1, further comprising:
   a conformal coating between the barrier layer and the energy source, the electro-active device, and the circuitry.

6. The biomedical device according to claim 1, further comprising:
   a conformal coating between the barrier layer and the molded layer.

7. The biomedical device according to claim 1, further comprising:
   a coating layer on the outer surface of the molded layer.

8. The biomedical device according to claim 1, further comprising:
   an embedment surrounding the molded layer.

9. The biomedical device according to claim 1, wherein the biomedical device is a contact lens and the electro-active device comprises a liquid crystal variable optic.

10. The biomedical device according to claim 1, wherein the molded layer is hydrophilic.

11. The biomedical device according to claim 1, wherein the molded layer comprises a polymer.

12. The biomedical device according to claim 11, wherein the polymer comprises at least one of acrylics, amides, imides, carbonates, diener, esters, ethers, fluorocarbons, olefins, styrenes, vinyl acetals, vinyl and vinylidene chlorides, vinyl esters, vinyl ethers and ketones, vinylpyridine, and vinypyrrolidone polymers.

13. The biomedical device according to claim 11, wherein the polymer comprises epoxy or parylene.

* * * * *